United States Patent
Sherman et al.

(10) Patent No.: US 7,261,000 B2
(45) Date of Patent: Aug. 28, 2007

(54) METHODS OF ASSESSING CHARACTERISTICS OF FIBROUS SUBSTRATES AND TREATING FIBROUS SUBSTRATES

(75) Inventors: Faiz Feisal Sherman, West Chester, OH (US); Vladimir Gartstein, Cincinnati, OH (US); Helen Rochelle Kemp, Hamilton, OH (US); Thomas A. Sturgis, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 131 days.

(21) Appl. No.: 11/113,468

(22) Filed: Apr. 25, 2005

(65) Prior Publication Data

US 2005/0238793 A1    Oct. 27, 2005

Related U.S. Application Data

(60) Provisional application No. 60/565,696, filed on Apr. 26, 2004.

(51) Int. Cl.
*G01N 3/00* (2006.01)

(52) U.S. Cl. .............................. 73/789; 73/160; 73/764

(58) Field of Classification Search .................. 73/160, 73/789, 764, 794, 828, 795, 817, 830, 831, 73/834, 837
See application file for complete search history.

(56) References Cited

U.S. PATENT DOCUMENTS

| | | | |
|---|---|---|---|
| 3,755,733 A | | 8/1973 | Vankoughnett |
| 4,358,731 A | | 11/1982 | Steinbrecher |
| 4,364,008 A | | 12/1982 | Jacques |
| 4,378,168 A | | 3/1983 | Kuisma |
| 4,546,311 A | | 10/1985 | Knochel |
| 4,744,154 A | | 5/1988 | Bollinger |
| 4,834,968 A | | 5/1989 | Bolich, Jr. |
| 4,877,042 A | | 10/1989 | Downey |
| 5,159,838 A | * | 11/1992 | Lynnworth ............ 73/644 |
| 5,165,287 A | * | 11/1992 | Manahan, Sr. ........ 73/851 |
| 5,256,978 A | | 10/1993 | Rose |
| 5,315,258 A | * | 5/1994 | Jakkula et al. ........ 324/640 |
| 5,461,925 A | | 10/1995 | Nguyen et al. |
| 5,502,393 A | | 3/1996 | Yamaguchi et al. |
| 5,568,691 A | | 10/1996 | Rubin |
| 5,610,527 A | | 3/1997 | Yamaguchi |
| 5,767,409 A | | 6/1998 | Yamaguchi |
| 5,767,685 A | * | 6/1998 | Walker ................ 324/640 |
| 5,857,379 A | | 1/1999 | Lulofs et al. |
| 5,864,240 A | | 1/1999 | Hirai et al. |
| 5,969,254 A | | 10/1999 | Yamaguchi |
| 6,040,282 A | | 3/2000 | Guskey et al. |
| 6,237,417 B1 | * | 5/2001 | Lonsdale et al. ....... 73/579 |
| 6,248,317 B1 | | 6/2001 | Snyder et al. |
| 6,490,492 B1 | | 12/2002 | Fertig et al. |
| 6,854,322 B2 | * | 2/2005 | Sherman et al. ....... 73/73 |

FOREIGN PATENT DOCUMENTS

| | | |
|---|---|---|
| DE | 3938391 A1 | 7/1990 |
| EP | 0 701 118 A2 | 3/1996 |
| EP | 0 902 276 A2 | 3/1999 |
| EP | 0 926 487 A1 | 6/1999 |
| EP | 0 619 485 B1 | 12/1999 |
| EP | 0990 887 A2 | 4/2000 |
| EP | 0 792 113 B1 | 12/2001 |
| JP | 51125567 A2 | 11/1976 |
| JP | 54136972 A2 | 10/1979 |
| JP | 57-163860 A | 10/1982 |
| JP | 58211624 A2 | 12/1983 |
| JP | 58215546 A2 | 12/1983 |
| JP | 59018455 A2 | 1/1984 |
| JP | 59126943 A2 | 7/1984 |
| JP | 60198449 A2 | 10/1985 |
| JP | 61194341 A2 | 8/1986 |

(Continued)

OTHER PUBLICATIONS

XP-009042395, Matsuda, K., et al., "High-Q Active Inductor and Its LC Oscillator Application", Technical Report of IEICE, Tokyo, Japan, vol. NPL2001-39, pp. 37-41 (Jul. 2001). ISSN: 0913-5685.

(Continued)

*Primary Examiner*—Hezron Williams
*Assistant Examiner*—Jacques M Saint-Surin
(74) *Attorney, Agent, or Firm*—Idris N. McKelvey

(57) ABSTRACT

A method of assessing damage of a fibrous substrate comprises the steps of: (a) providing said fibrous substrate having a length, a root end, and a tip end; (b) providing a means for assessing substrate moisture content; (c) using said means for assessing substrate moisture content to obtain at least a first measured moisture content value for said fibrous substrate at a first position along the length of said fibrous substrate and a second measured moisture content value for said fibrous substrate at a second position along the length of said fibrous substrate; (d) comparing said measured moisture content values with each other to obtain a measured moisture content differential; and (e) correlating said measured moisture content differential to a substrate damage value for said fibrous substrate. A method of treating a fibrous substrate comprises the steps of: (a) assessing damage of the fibrous substrate according to the method described above to obtain a correlated substrate damage value for the fibrous substrate; (b) using the correlated substrate damage value to select at least one appropriate substrate treatment composition; and (c) applying the appropriate substrate treatment composition to the fibrous substrate.

9 Claims, No Drawings

FOREIGN PATENT DOCUMENTS

| | | | |
|---|---|---|---|
| JP | 61195341 A2 | 8/1986 |
| JP | 61221639 A2 | 10/1986 |
| JP | 61221640 A2 | 10/1986 |
| JP | 61221641 A2 | 10/1986 |
| JP | 61221642 A2 | 10/1986 |
| JP | 61251756 A2 | 11/1986 |
| JP | 61251759 A2 | 11/1986 |
| JP | 63075562 A2 | 4/1988 |
| JP | 63163143 A | 7/1988 |
| JP | 2283313 A2 | 11/1990 |
| JP | 3000008 A2 | 1/1991 |
| JP | 3195508 A2 | 8/1991 |
| JP | 4038463 A2 | 2/1992 |
| JP | 4058903 A2 | 2/1992 |
| JP | 4193203 A2 | 7/1992 |
| JP | 4336002 A2 | 11/1992 |
| JP | 5007508 A2 | 1/1993 |
| JP | 5095813 A2 | 4/1993 |
| JP | 5184420 A2 | 7/1993 |
| JP | 5192216 A2 | 8/1993 |
| JP | 5192217 A2 | 8/1993 |
| JP | 5196506 A2 | 8/1993 |
| JP | 5293010 A2 | 11/1993 |
| JP | 7088009 A2 | 4/1995 |
| JP | 2883165 B2 | 4/1999 |
| JP | 11322547 A2 | 11/1999 |
| JP | 2003254926 A | 9/2003 |
| SU | 1453275 A | 1/1989 |
| WO | WO97/09898 | 3/1997 |
| WO | WO98/21818 | 5/1998 |

OTHER PUBLICATIONS

Abrosimova, E.B., et al., "Amplitude UHF Humidity Meter for Solid And Powdered Materials,"*Measurement Techniques*, vol. 39, No. 11, Nov. 1, 1996, pp. 1162-1165.

Nagata, H., "Hair Moisture Meter HC-1000", *Sharp Technical Journal*, 1985, Japan, No. 33, pp. 151-152.

Kupfer, K., et al., "Materialfeuchtemessung mit Mikrowellen (Moisture measurement with microwaves)", *Technisches Messen TM*, R. Oldenbourg Verlag, Munchen, Germany, vol. 59, No. 3, Mar. 1, 1992, pp. 110-115.

* cited by examiner

METHODS OF ASSESSING CHARACTERISTICS OF FIBROUS SUBSTRATES AND TREATING FIBROUS SUBSTRATES

CROSS REFERENCE TO RELATED APPLICATION

This application claims the benefit of U.S. Provisional Application No. 60/565,696, filed Apr. 26, 2004.

FIELD OF THE INVENTION

The present invention relates to methods of assessing characteristics of fibrous substrates and methods of treating fibrous substrates. More particularly, one aspect of the present invention relates to methods of assessing characteristics of a fibrous substrate comprising making a correlation between moisture content of the fibrous substrate and other physical and cosmetic characteristics of the fibrous substrate. Another aspect of the present invention, more particularly, relates to methods of treating a fibrous substrate comprising selecting an appropriate substrate treatment composition based on an assessment of characteristics of the fibrous substrate.

BACKGROUND OF THE INVENTION

Methods of treating fibrous substrates generally may involve the application of at least one of a variety of treatment compositions. Such treatment compositions may be selected to provide or to restore certain desired physical or cosmetic characteristics to the fibrous substrate. However, unless an appropriate treatment composition is selected, the desired physical or cosmetic characteristics may not be obtained.

In the case of treating fibrous substrates comprising keratinous fibers, such as human hair, treatment compositions generally include shampoos, conditioners, colorants, styling compositions, and the like. Manufacturers of these hair treatment compositions may provide multiple versions of a type or brand of hair treatment composition, wherein each of the multiple versions is specifically designed to target a need or demand which is characteristic of a specific consumer segment and which may be based on physical or cosmetic differences of hair generally found between respective consumer segments. For example, a single brand of hair conditioner may offer a first version designed to deliver a level of conditioning appropriate for dry and damaged hair and a second version designed to deliver a level of conditioning appropriate for oily hair.

However, when a consumer is faced with the task of selecting a hair treatment composition from among the multiple versions of a hair treatment composition brand, the consumer may unknowingly select a version which is not designed to provide the characteristics desired by the consumer. In such a case, the consumer may be dissatisfied with the results of the selected version of the hair treatment composition brand. As a result of the consumer's dissatisfaction, the consumer subsequently may refuse to select any of the versions of that same hair treatment composition brand even though another version of that hair treatment composition brand may provide the consumer's desired hair characteristics. The occurrence of such circumstances, in turn, may lead to unnecessary loss of sales of the particular hair care composition brand for the manufacturer. Accordingly, there exists a need for a method of treating a fibrous substrate which comprises the selection of an appropriate substrate treatment composition that is designed to provide or to restore desired physical or cosmetic characteristics to the fibrous substrate.

In turn, there exists a need for a method of assessing characteristics of a fibrous substrate which easily, quickly, accurately, and economically provides information about the physical or cosmetic characteristics of the fibrous substrate. Such information may then be used to guide selection of an appropriate substrate treatment composition in a method of treating a fibrous substrate. However, known methods of assessing characteristics of a fibrous substrate do not provide accurate and consistent results.

For fibrous substrates comprising keratinous fibers, such as human hair, methods of assessing a physical or cosmetic characteristic of the hair typically involve taking a single measurement of some parameter associated with the characteristic at some arbitrary position along the length of the hair. That single measurement is then often compared against a known value of that parameter for a separate control sample of hair having that characteristic. Such assessment methods may not be accurate or may not provide consistent and repeatable results because they fail to account for at least several factors. First, many physical or cosmetic characteristics of hair are affected by environmental conditions, such as temperature and relative humidity. Second, a single physical or cosmetic characteristic of hair may vary along the length of that hair from root to tip. Third, many physical or cosmetic characteristics of hair may inherently vary among different individuals or groups of individuals (i.e., one "control value" may not fit all individuals). As a result, a need still exists for a method of assessing characteristics of a fibrous substrate that provides accurate and consistent results by accounting for the above factors.

SUMMARY OF THE INVENTION

It has now been discovered that an accurate and repeatable assessment of damage and other physical or cosmetic characteristics of a fibrous substrate, including fibrous substrates comprising keratinous fibers such as hair, is achieved by comparing the value of a parameter, such as substrate moisture content, for at least a first position along the length of the fibrous substrate with the value of the parameter for at least a second position along the length of the fibrous substrate. By comparing the at least two measured values with each other, as opposed to comparing a single measured value with a known control value, a measured parameter differential profile is obtained which is correlated to a damage or other characteristic assessment. This assessment is independent of the effects of such variables as environmental conditions during measurement, because the correlation is based upon the relative differences between the at least two values for each corresponding position along the length of the fibrous substrate.

A method of assessing damage of a fibrous substrate is provided, said method comprising the steps of: (a) providing said fibrous substrate having a length, a root end, and a tip end; (b) providing a means for assessing substrate moisture content; (c) using said means for assessing substrate moisture content to obtain at least a first measured moisture content value for said fibrous substrate at a first position along the length of said fibrous substrate and a second measured moisture content value for said fibrous substrate at a second position along the length of said fibrous substrate; (d) comparing said measured moisture content values with each other to obtain a measured moisture content differential; and (e) correlating said measured moisture content differential to a substrate damage value for said fibrous substrate.

In another aspect of the invention, a method of treating a fibrous substrate is provided, said method comprising the steps of: (a) assessing damage of the fibrous substrate according to the method described above to obtain a correlated substrate damage value for the fibrous substrate; (b) using the correlated substrate damage value to select at least one appropriate substrate treatment composition; and (c) applying the appropriate substrate treatment composition to the fibrous substrate.

DETAILED DESCRIPTION OF THE INVENTION

While the specification concludes with claims which particularly point out and distinctly claim the invention, it is believed the present invention will be better understood from the following description.

I. Methods of Assessing Damage and Other Characteristics of a Fibrous Substrate

The present invention provides methods of assessing damage as well as other characteristics of a fibrous substrate, wherein the methods comprise making a correlation between moisture content of the fibrous substrate and other physical and cosmetic characteristics of the fibrous substrate.

A measurement of the moisture content of the fibrous substrate is made for at least two positions along the length of the fibrous substrate. However, several such measurements at various distances along the length of the fibrous substrate can be produced. Such a plurality of measurements provides a measured moisture content differential profile, and, thus, a correlated profile of the exemplary characteristics of the fiber. Such a profile provides a better, and more accurate, indication of overall condition of the fibrous substrate because the correlation is based upon the relative differences between the at least two values for each corresponding position along the length of the fibrous substrate. The fibrous substrate serves as its own control.

According to the present invention, a method of assessing damage of a fibrous substrate comprises the steps of: (a) providing said fibrous substrate having a length, a root end, and a tip end; (b) providing a means for assessing substrate moisture content; (c) using said means for assessing substrate moisture content to obtain at least a first measured moisture content value for said fibrous substrate at a first position along the length of said fibrous substrate and a second measured moisture content value for said fibrous substrate at a second position along the length of said fibrous substrate; (d) comparing said measured moisture content values with each other to obtain a measured moisture content differential; and (e) correlating said measured moisture content differential to a substrate damage value for said fibrous substrate.

In one embodiment of the present invention, the means for assessing substrate moisture content is used to obtain one or more additional measured moisture content values for the fibrous substrate at corresponding additional positions along the length of the fibrous substrate.

In another embodiment of the present invention, the first position along the length of the fibrous substrate is about the root end of the fibrous substrate and the second position along the length of the fibrous substrate is about the tip end of the fibrous substrate. For example, in the case of a fibrous substrate comprising keratinous fibers, such as human hair, the root end of the fibrous substrate is at the roots of the hair and the tip end of the fibrous substrate is at the tips of the hair.

In a further embodiment of the present invention, the means for assessing substrate moisture content is used to obtain one or more additional measured moisture content values for the fibrous substrate at corresponding additional positions along the length of the fibrous substrate and between the root and tip ends of the fibrous substrate.

The determination of moisture content in a fibrous substrate is used to quantify various physical and cosmetic characteristics of the substrate. Fibrous substrates, such as human hair, generally comprise complex proteins called alpha keratins. Alpha keratin fibers, including wool and hair, have a special affinity for water. Hair is hygroscopic and permeable and can absorb water from the environment. Under normal conditions, water accounts for about 12% to 15% of the composition of hair. Further, hair can absorb more than 30% of its own weight in water. Typically, hair absorbs about 30% of its own weight of water at saturation. If the hair is damaged, this percentage can approach 45%. However, the ability of damaged hair to retain water within the hair fibers that gives hair its healthy appearance is reduced.

As a result of this interaction with water, nearly all physical characteristics of keratinous fibers may be modified in the presence of water. Examples include variations in length and diameter, changes in internal viscosity, hair holding and setting properties, hair strength, and electro-optic properties. Further, characteristics such as damage, shine, color, luster, smoothness, combing ease, frizz/fly-away, volume/body, and strength may be determined.

How a correlation may be made between a measured moisture content differential of a fibrous substrate, such as human hair, and each of several exemplified characteristics is provided in the following Examples 1 through 5.

EXAMPLE 1

Hair Moisture Content and Hair Damage

A correlation made between the moisture content of hair and hair damage is made based on the following observations and relationships.

Hair is damaged on a daily basis through common grooming and styling habits such as brushing, combing, and chemical treatments, as well as environmental factors such as sun exposure. An increase in scale raising, removal of larger chunks of scales, cuticle lifting, and other types of damaging effects occur as the grooming action moves closer to the tip of the hair because the cell membrane complex and other vital structures are weaker near the tip of the hair. Therefore, as hair grows, there is a gradient of damage level from root to tip with the tip having been exposed to more of the damaging effects than the root. Further, the rate of damage to hair accelerates as the damaging effects move from the root to the tip of the hair.

To determine a relationship between the amount of hair damage and the length of hair from the scalp, 100 hairs are sampled from 12-inch hair switches and are studied under a microscope. The switches are made from blended hair from many individuals and the hair condition is as sourced from people's heads. The occurrence of damage is assessed at 0, 3, 6, 9, and 12 inches from the root of the switch on each fiber. Damage to the hair in the forms of uplifted cuticles, cuticle bubbling, broken/worn cuticles, and missing cuticles (with exposed cortex), are identified by visual grading under an SEM microscope. Exemplary hair damage results are shown below in Table 1.

TABLE 1

Fiber Damage Level Compared to
Relative Distance from Hair Root

| Length from Root End of Switch (inches) | Percentage of Fibers with Damage |
|---|---|
| 0" | 11% |
| 3" | 14% |
| 6" | 18% |
| 9" | 42% |
| 12" | 47% |

As can be seen from Table 1, as the distance from the root increases, the level of damage evidenced increased.

To determine a relationship between moisture content and length of hair from scalp, any suitable means of assessing moisture content of a fibrous substrate may be used. For example, an electronic device comprising a high frequency signal generator and a high-Q LC circuit having a resonance frequency can be used to measure the moisture content of the 12-inch hair switches referenced above. Suitable means for assessing moisture content of a fibrous substrate also include an electronic device comprising a directional coupler sensor, as described in U.S. Pat. No. 6,854,322 to Sherman et al. Using such a suitable means of assessing moisture content to obtain substrate moisture content values, it can be seen that, generally, as the distance from the root increases, the moisture content value decreases.

It is believed that these data suggest that the amount of moisture in the hair switch is a function of damage to the hair, and, thus, a correlation between hair moisture content and hair damage may be established. As shown in Table 1, the level of damage to the hair increases with distance from the root. Further, based on the substrate moisture content values which can be obtained with a means for assessing moisture content, it can be seen that the moisture content of the hair decreases with distance from the root. Thus, it is believed that an increase in hair damage leads to a loss of moisture in the hair. Stated differently, the moisture content of the hair is inversely proportional to the amount of damage to the hair. However, the amount of the difference between the moisture content at the root of the hair and the moisture content at the tip of the hair is proportional to the amount of damage of the hair. As a result, the differential in measured moisture content for various positions along the length of the hair can be correlated to an amount of overall hair damage.

It is also believed that while damaged hair loses moisture content, the moisture flux of the hair continues to be high. As such, this dynamic change may also be used to assess damage.

The relationship between hair moisture content and hair damage is determined by taking multiple hair switches with known variances in hair damage, measuring the moisture content of the hair switches, and graphically plotting the moisture content as a function of hair damage. A best-fit equation is used to describe the empirical relationship between moisture content and hair damage. Methods for determining a best-fit equation are known in the art. As a result, an assessment of hair damage is made through an assessment of hair moisture content.

EXAMPLE 2

Hair Moisture Content, Hair Damage and Hair Shine/Luster

A correlation made between moisture content of hair, hair damage, and hair shine/luster is based on the observations and relationships described above in Example 1 and the following observations and relationships.

The greater the damage to a hair fiber, the less shine the hair will have, providing it with a more dull appearance. This is caused by the cuticle becoming uplifted and the hair surface becoming roughened with increased damage. This increases the light scatter thereby making the hair appear duller than hair that is smooth and has a healthier condition. Because abrasion decreases hair shine (specular/diffuse reflectance), the dulling effect increases with increasing abrasion. Teasing (back-combing) hair and other abrasive actions such as vigorous combing or brushing delusters the hair by breaking scale edges and creating more irregularities on the fiber surface. These actions dull hair by increasing diffuse scattering.

When a correlation is made between moisture content of hair and hair damage as described above, moisture content of hair is correlated indirectly to an assessment of hair shine as a function of hair damage. Hair shine is measured instrumentally using a Murakami GP-200 633 nm He—Ne Laser Goniophotometer. Intensity measurements as a function of incident angle are used to plot a light-intensity distribution. As hair becomes more damaged, the light reflected off of the hair surface is increasingly scattered, and the intensity distribution becomes broadened and less intense. R. F. Stamm et al., J. Soc. Cosmet. Chem. 28:571 (1977), provide that Hair Shine=(S−D)/D where S is the specular reflectance and D is the diffuse reflectance as measured by the goniophotometer.

To correlate hair shine to hair damage, a 12-inch hair switch of known damage differences from root to tip is sampled and hair shine is measured instrumentally with a goniophotometer at several lengths of the hair switch. The measured hair shine values corresponding to the known damage level for the respective length of hair result in an empirical relationship of hair shine as a function of hair damage. A best-fit equation is used to describe the relationship between hair shine and hair damage. Methods for determining a best-fit equation are known in the art.

Using the relationship between hair moisture content and hair damage described above in Example 1, an assessment of hair shine is made though an assessment of hair moisture content.

EXAMPLE 3

Hair Moisture Content, Hair Damage and Hair Smoothness/Comb Ease

A correlation made between moisture content of hair, hair damage, and hair smoothness/comb ease is based on the observations and relationships described above in Example 1 and the following observations and relationships.

The greater damage to the hair fiber, the greater the increase in the surface friction of the hair due to uplifted and broken cuticles which increase the roughness of the hair. The cuticle of human hair contains smooth unbroken scale edges at the root end near the scalp. Cuticle damage is evidenced by broken scale edges which are observed several centimeters away from the scalp and which are caused by weathering and mechanical damage from effects of normal grooming actions, such as combing, brushing, and shampooing. As hair damage increases hair fiber friction through uplifted cuticle and broken scale edges, hair-on-hair friction is more important to combing ease than hair-on-comb friction. Therefore, a measure of hair damage can also accurately provide an assessment of hair smoothness/comb ease.

When a correlation is made between moisture content of hair and hair damage as described above, moisture content of hair is correlated indirectly to an assessment of hair smoothness/comb ease as a function of hair damage. Hair smoothness/comb ease is measured through frictional analysis/combing force measurements using an INSTRON 5542 Electromechanical Tensile Tester. A comb is attached to the tensile tester and is drawn through a hair switch. Combing force measurements are recorded. An increase in hair damage results in an increase in the combing force because of increased surface roughness of damaged hair.

To correlate hair smoothness/comb ease to hair damage, a 12-inch hair switch of known damage differences from root to tip is sampled and the combing force is measured at several lengths of the hair switch. The measured combing force values corresponding to the known damage level for the respective length of hair result in an empirical relationship of hair smoothness/comb ease as a function of hair damage. A best-fit equation is used to describe the relationship between hair shine and hair damage. Methods for determining a best-fit equation are known in the art.

Using the relationship between hair moisture content and hair damage described above in Example 1, an assessment of hair smoothness/comb ease is made though an assessment of hair moisture content.

EXAMPLE 4

Hair Moisture Content and Hair Frizz/Fly-aways

A correlation made between moisture content of hair and hair frizz/fly-aways is based on the following observations and relationships.

The moisture content of hair directly impacts the frizz/fly-away characteristics of hair. This is because the moisture content of hair generally provides a larger influence on static charge than any other variable, as a direct action of moisture content is on the electrical resistance (conductance) of hair. Thus, increasing moisture content increases the conductivity of the fiber surface so that it is less prone to develop a static charge.

Moisture content of hair is correlated directly to an assessment of hair frizz/fly-aways. Hair switches are equilibrated in a range of humidity environments and the moisture levels of the switches are measured as described above in Example 1. Each switch is combed in a controlled manner and imaged in a controlled manner for the frizz/fly-away effect created. These images are quantitatively analyzed for frizz/fly-aways through fiber count or pixel area count of the frizz/fly-away hair separated from the switch. The measured hair frizz/fly-aways corresponding to the measured moisture content result in an empirical relationship of hair frizz/fly-aways as a function of hair moisture content. A best-fit equation is used to describe the relationship between known moisture levels of the switches and the resulting hair frizz/fly-aways. Methods for determining a best-fit equation are known in the art.

Accordingly, an assessment of hair frizz/fly-aways is made though an assessment of hair moisture content.

EXAMPLE 5

Hair Moisture Content and Hair Strength

A correlation made between moisture content of hair and hair strength is based on the following observations and relationships.

There are variations in both length and diameter, as well as changes in the internal viscosity, of hair that correspond to changes in moisture content. Further, as a keratin fiber is stretched, it is more prone to induce uneven cortical fracturing (damage) in the dry state (below 90% relative humidity). This is caused by the cortex of hair being much less extensible than the cuticle when the fiber is dry.

The swelling behavior of the hair fiber is related to its structure. In other words, an increase in fiber diameter is seen with an increase in moisture uptake. Fiber swelling is believed to have a direct relationship to both wet and dry tensile properties. These tensile properties are proportional to fiber diameter and are determined from fiber diameter. The linear density is proportional to the cross sectional area and diameter of the fiber. As a result, the tensile properties of the fiber are proportional to the fiber diameter. The percentage of a fiber which swells is proportional to the amount of water absorbed by the fiber. Thus, fiber moisture content can be correlated to fiber tensile strength.

It is also believed that a regular increase in extensibility (percent extension to break) occurs with increasing relative humidity for wool and that this same relationship holds true for hair. In hair, as the relative humidity increases, the extensibility of hair increases, and the elastic modulus decreases. Because wool and hair both quantitatively, to a nearly identical factor, bind water as a function of relative humidity, there may be similar relative humidity stress strain relationship for hair as there is in wool.

Additionally, the torsional behavior of hair is dependent upon the external cuticle layers of the hair fiber. Based on the level of damage to the hair fiber, it is believed that water will impact the torsional behavior differently. Further, it is believed that hair damaged due to permanent waving, bleaching, or dying is less rigid, less stiff, than that of virgin (chemically unaltered) hair in the dry state.

Similar to torsional behavior, fiber stiffness can also vary with relative humidity. As the moisture content of hair increases, hair fiber stiffness decreases. This same relationship can be true for rigidity. Rigidity is the torque required to produce a twist of one turn per centimeter. Rigidity is analogous to stiffness in bending. With an increase in hair moisture, fiber stiffness decreases and as a result, fiber strength under stress will increase.

Moisture content of hair is correlated directly to an assessment of hair strength. Using an INSTRON 5542 Electromechanical Tensile Tester, hair switches are equilibrated in a range of humidity environments and the moisture levels of the switches are measured. Each switch then is tested for tensile strength at that given relative humidity. The measured tensile strength corresponding to the measured moisture content result in an empirical relationship of strength as a function of hair moisture content. A best-fit equation is used to describe the relationship between known moisture levels of the switches and the resulting hair strength. Methods for determining a best-fit equation are known in the art.

Accordingly, an assessment of hair strength is made though an assessment of hair moisture content.

II. Methods of Treating a Fibrous Substrate

In another aspect of the present invention, a method of treating a fibrous substrate is provided, said method comprising the steps of: (a) assessing damage of the fibrous substrate according to the method described above to obtain a correlated substrate damage value for the fibrous substrate; (b) using the correlated substrate damage value to select at least one appropriate substrate treatment composition; and (c) applying the appropriate substrate treatment composition to the fibrous substrate.

As used herein, an "appropriate substrate treatment composition" is a composition which provides or restores a fibrous substrate with the physical or cosmetic characteristics desired by the one who performs the method of treating. In the case of treating fibrous substrates comprising keratinous fibers, such as human hair, treatment compositions generally include shampoos, conditioners, colorants, styling compositions, and the like.

The fibers that may be assessed and treated using the methods of the present invention may be comprised of a variety of natural materials wherein the dielectric constant of the fiber is significantly different from that of water. By natural is meant that the materials are derived from plants, animals, insects or byproducts of plants, animals, and insects.

Non-limiting examples of natural fibers useful in the present invention are silk fibers, keratin fibers and cellulosic fibers. Non-limiting examples of keratin fibers include those selected from the group consisting of wool fibers, camel hair fibers, human hair and the like. Non-limiting examples of cellulosic fibers include those selected from the group consisting of wood pulp fibers, cotton fibers, hemp fibers, jute fibers, flax fibers, and mixtures thereof.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of assessing damage of a fibrous substrate, said method comprising the steps of:
   a) providing said fibrous substrate having a length, a root end, and a tip end;
   b) providing a means for assessing substrate moisture content;
   c) using said means for assessing substrate moisture content to obtain at least a first measured moisture content value for said fibrous substrate at a first position along the length of said fibrous substrate and a second measured moisture content value for said fibrous substrate at a second position along the length of said fibrous substrate;
   d) comparing said measured moisture content values with each other to obtain a measured moisture content differential; and
   e) correlating said measured moisture content differential to a substrate damage value for said fibrous substrate.

2. A method of assessing damage of a fibrous substrate according to claim 1, wherein said means for assessing substrate moisture content is used to obtain one or more additional measured moisture content values for said fibrous substrate at corresponding additional positions along the length of said fibrous substrate.

3. A method of assessing damage of a fibrous substrate according to claim 1, wherein said first position along the length of said fibrous substrate is about said root end of said fibrous substrate and said second position along the length of said fibrous substrate is about said tip end of said fibrous substrate.

4. A method of assessing damage of a fibrous substrate according to claim 3, wherein said means for assessing substrate moisture content is used to obtain one or more additional measured moisture content values for said fibrous substrate at corresponding additional positions along the length of said fibrous substrate and between said mat and tip ends of said fibrous substrate.

5. A method of assessing damage of a fibrous substrate according to claim 1, wherein said fibrous substrate comprises fibers selected from the group consisting of silk fibers, keratin fibers, and cellulosic fibers.

6. A method of assessing damage of a fibrous substrate according to claim 5, wherein said fibrous substrate comprises keratin fibers selected from the group consisting of human hair and animal hair.

7. A method of assessing damage of a fibrous substrate according to claim 1, wherein said means for assessing substrate moisture content is an electronic device.

8. A method of treating a fibrous substrate, said method comprising the steps of:
   a) assessing damage of said fibrous substrate according to the method of claim 1;
   b) using said correlated substrate damage value to select at least one appropriate substrate treatment composition; and
   c) applying said appropriate substrate treatment composition to said fibrous substrate.

9. A method of treating a fibrous substrate according to claim 8, wherein said appropriate substrate treatment composition is selected from the group consisting of shampoos, conditioners, colorants, and styling compositions.

* * * * *